(12) United States Patent
Riddle et al.

(10) Patent No.: US 7,708,731 B2
(45) Date of Patent: May 4, 2010

(54) ELECTROTRANSPORT DELIVERY DEVICE WITH VOLTAGE BOOSTING CIRCUIT

(75) Inventors: Thomas A. Riddle, Sunnyvale, CA (US); Larry A. McNichols, Coon Rapids, MN (US); John D. Badzinski, Coon Rapids, MN (US)

(73) Assignee: Alza Corporation, Vacaville, CA (US)

( * ) Notice: Subject to any disclaimer, the term of this patent is extended or adjusted under 35 U.S.C. 154(b) by 816 days.

(21) Appl. No.: 10/999,504

(22) Filed: Nov. 30, 2004

(65) Prior Publication Data

US 2005/0075623 A1 Apr. 7, 2005

Related U.S. Application Data

(60) Division of application No. 10/253,419, filed on Sep. 25, 2002, now Pat. No. 6,842,640, which is a continuation of application No. 09/482,526, filed on Jan. 14, 2000, now abandoned, which is a continuation of application No. 08/939,921, filed on Sep. 29, 1997, now Pat. No. 6,035,234, which is a continuation of application No. 08/460,322, filed on Jun. 2, 1995, now abandoned.

(51) Int. Cl.
*A61M 31/00* (2006.01)

(52) U.S. Cl. .......................................... 604/501; 604/20

(58) Field of Classification Search .................... 604/20, 604/501; 600/547
See application file for complete search history.

(56) References Cited

U.S. PATENT DOCUMENTS

| | | | |
|---|---|---|---|
| 3,618,601 A | 11/1971 | Richardson | |
| 3,991,755 A | 11/1976 | Vernon et al. | |
| 4,019,510 A | 4/1977 | Ellis | |
| 4,141,359 A | 2/1979 | Jacobsen et al. | |
| 4,149,533 A | 4/1979 | Ishikawa et al. | |
| 4,250,878 A | 2/1981 | Jacobsen et al. | |
| 4,292,968 A | 10/1981 | Ellis | |
| 4,301,794 A | 11/1981 | Tapper | |
| 4,340,047 A | 7/1982 | Tapper et al. | |
| 4,383,529 A | 5/1983 | Webster et al. | |
| 4,398,545 A | 8/1983 | Wilson | |
| 4,406,658 A | 9/1983 | Lattin et al. | |
| 4,456,012 A | 6/1984 | Lattin | |
| 4,457,748 A | 7/1984 | Lattin et al. | |
| 4,689,039 A | 8/1987 | Masaki | |
| 4,725,263 A | 2/1988 | McNichols et al. | |
| 4,764,164 A | 8/1988 | Sasaki | |
| 4,786,277 A | 11/1988 | Powers et al. | |
| 4,786,278 A | 11/1988 | Masaki | |
| 4,792,702 A | 12/1988 | Masaki | |
| 4,808,152 A | 2/1989 | Sibalis | |

(Continued)

FOREIGN PATENT DOCUMENTS

AU    7588691    5/1991

(Continued)

*Primary Examiner*—Mark W Bockelman
(74) *Attorney, Agent, or Firm*—Michael J. Atkins (57) ABSTRACT

An electrotransport device (10) for delivering therapeutic agents includes an adjustable voltage boos multiple controller (100, 200) for boosting the voltage from a power source (102, 202) to a working voltage $V_w$ having a value just sufficient to provide the desired therapeutic current level $I_f$ through the electrodes (108, 112), at least of which contains the therapeutic agent to be delivered.

5 Claims, 5 Drawing Sheets

U.S. PATENT DOCUMENTS

| | | |
|---|---|---|
| 4,822,334 A | 4/1989 | Tapper |
| 4,850,956 A | 7/1989 | Bontemps |
| 4,855,243 A | 8/1989 | Simic-Glavaski |
| 4,866,442 A | 9/1989 | Steim et al. |
| 4,878,892 A | 11/1989 | Sibalis et al. |
| 4,931,046 A | 6/1990 | Newman |
| 4,942,883 A | 7/1990 | Newman |
| 4,997,418 A | 3/1991 | DeMartini |
| 5,006,108 A | 4/1991 | LaPrade |
| 5,013,293 A | 5/1991 | Sibalis |
| 5,042,975 A | 8/1991 | Chien et al. |
| 5,047,007 A | 9/1991 | McNichols et al. |
| 5,135,478 A | 8/1992 | Sibalis et al. |
| 5,135,480 A | 8/1992 | Bannon et al. |
| 5,152,758 A | 10/1992 | Kaetsu et al. |
| 5,160,316 A | 11/1992 | Henley |
| 5,169,384 A | 12/1992 | Bosniak et al. |
| 5,207,752 A | 5/1993 | Sorenson et al. |
| 5,213,568 A | 5/1993 | Lattin et al. |
| 5,224,927 A | 7/1993 | Tapper |
| 5,224,928 A | 7/1993 | Sibalis et al. |
| 5,246,418 A | 9/1993 | Haynes et al. |
| 5,250,022 A | 10/1993 | Chien |
| 5,254,081 A | 10/1993 | Maurer et al. |
| 5,256,137 A | 10/1993 | Sage, Jr. |
| 5,283,441 A | 2/1994 | Fabian |
| 5,286,254 A | 2/1994 | Shapland et al. |
| 5,306,235 A | 4/1994 | Haynes |
| 5,312,325 A | 5/1994 | Sibalis |
| 5,314,502 A | 5/1994 | McNichols |
| 5,328,452 A | 7/1994 | Sibalis |
| 5,328,454 A | 7/1994 | Sibalis |
| 5,336,168 A | 8/1994 | Sibalis |
| 5,374,242 A | 12/1994 | Haak et al. |
| 5,426,387 A | 6/1995 | Teillaud et al. |
| 5,499,967 A | 3/1996 | Teillaud et al. |
| 5,540,654 A | 7/1996 | Riviere et al. |
| 5,637,084 A | 6/1997 | Kontturi et al. |
| 6,035,234 A | 3/2000 | Riddle et al. |
| 6,391,015 B1 | 5/2002 | Millot |
| 6,842,640 B2 * | 1/2005 | Riddle et al. .................. 604/20 |
| 2001/0029347 A1 | 10/2001 | Kasano |

FOREIGN PATENT DOCUMENTS

| | | |
|---|---|---|
| AU | 6833090 | 6/1991 |
| DE | 4 028 125 | 7/1991 |
| EP | 0 092 015 | 10/1983 |
| EP | 0 230 749 | 8/1987 |
| EP | 0 308 572 | 3/1989 |
| EP | 0558409 A1 | 2/1993 |
| EP | 0 547 482 | 6/1993 |
| EP | 0847775 A1 | 6/1998 |
| FR | 0 558 409 | 9/1993 |
| GB | 2 041 752 | 9/1980 |
| GB | 2 064 178 | 6/1981 |
| GB | 2 219 210 | 12/1989 |
| WO | WO 91/15261 | 10/1991 |
| WO | 91/16943 | 11/1991 |
| WO | WO 93/03790 | 3/1993 |
| WO | 95/06497 A1 | 3/1995 |
| WO | 96/17651 | 6/1996 |
| WO | 96/30077 | 10/1996 |
| WO | 96/39222 | 12/1996 |
| WO | 99/30773 A1 | 6/1999 |

\* cited by examiner

ELECTROTRANSPORT DELIVERY DEVICE WITH VOLTAGE BOOSTING CIRCUIT

CROSS-REFERENCE TO RELATED APPLICATIONS

This application is a divisional of U.S. application Ser. No. 10/253,419, filed Sep. 25, 2002, now U.S. Pat. No. 6,842,640, which is a continuation of U.S. application Ser. No. 09/482,526, filed Jan. 14, 2000, now abandoned, which is a continuation of U.S. application Ser. No. 08/939,921, filed Sep. 29, 1997, now U.S. Pat. No. 6,035,234, which is a continuation of U.S. application Ser. No. 08/460,322, filed Jun. 2, 1995, now abandoned. The entire disclosures of these prior applications are hereby incorporated by reference.

TECHNICAL FIELD

This invention relates to an electrotransport device for transdermally or transmucosally delivering a beneficial agent (e.g., a drug) to a patient. More particularly, the invention relates to a portable or patient-worn electrotransport delivery device having an improved power supply.

BACKGROUND ART

The term "electrotransport" as used herein refers generally to the delivery of an agent (e.g., a drug) through a membrane, such as skin, mucous membrane, or nails, which delivery is induced or aided by the application of an electric potential. For example, a beneficial therapeutic agent may be introduced into the systemic circulation of an animal (e.g., a human) by electrotransport delivery through the skin.

The electrotransport process has been found to be useful in the transdermal administration of drugs including lidocaine hydrochloride, hydrocortisone, fluoride, penicillin, dexamethasone sodium phosphate, and many other drugs. Perhaps the most common use of electrotransport is in diagnosing cystic fibrosis by delivering pilocarpine salts iontophoretically. The pilocarpine stimulates sweat production; the sweat is collected and analyzed for its chloride content to detect the presence of the disease.

Presently known electrotransport devices use at least two electrodes, positioned in intimate contact with some portion of the body (e.g., the skin). A first electrode, called the active or donor electrode, delivers the therapeutic agent (e.g., a drug or a prodrug) into the body by electrotransport. The second electrode, called the counter or return electrode, closes an electrical circuit with the first electrode through the patient's body. A source of electrical energy, such as a battery, supplies electric current to the body through the electrodes. For example, if the therapeutic agent to be delivered into the body is positively charged (i.e., a cation), the anode will be the active electrode and the cathode will serve as the counter electrode to complete the circuit. If the therapeutic agent to be delivered is negatively charged (i.e., an anion), the cathode will be the donor electrode and the anode will be the counter electrode.

Alternatively, both the anode and cathode may be used to deliver drugs of opposite electrical charge into the body. In this situation, both electrodes are considered donor and counter electrodes. For example, the anode can simultaneously deliver a cationic therapeutic agent and act as a "counter" electrode to the cathode. Similarly, the cathode can simultaneously deliver an anionic therapeutic agent into the body and act as a "counter" electrode to the anode.

A widely used electrotransport process, electromigration (also called "iontophoresis"), involves the electrically induced transport of charged ions. Another type of electrotransport, electroosmosis, involves the flow of a liquid solvent from the donor reservoir, which liquid contains the agent to be delivered, under the influence of the applied electric field. Still another type of electrotransport process, electroporation, involves the formation of transiently existing pores in a biological membrane by the application of high voltage pulses. A therapeutic agent can in part be delivered through the skin by passive diffusion by reason of the concentration difference between the concentration of drug in the donor reservoir of the electrotransport device and the concentration of drug in the tissues of the patient's body. In any given electrotransport process, more than one of these processes may be occurring simultaneously to a certain extent. Accordingly, the term "electrotransport", as used herein, should be given its broadest possible interpretation so that it includes the electrically induced or enhanced transport of at least one therapeutic agent, whether charged, uncharged, or a mixture thereof.

The terms "drug" and "therapeutic agent" are used interchangeably and are intended to have their broadest interpretation, namely any therapeutically active substance that is delivered to a living organism to produce a desired, usually beneficial, effect. This includes therapeutic agents in all the major therapeutic areas including, but not limited to: anti-infectives such as antibiotics and antiviral agents; analgesics, including fentanyl, sufentanil, buprenorphine and analgesic combinations; anesthetics; anorexics; antiarthritics; antiasthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers.

Electrotransport is also useful in the controlled delivery of peptides, polypeptides, proteins and other macromolecules. These macromolecular substances typically have a molecular weight of at least 300 Daltons, and more typically have a molecular weight of 300-40,000 Daltons. Specific examples of peptides and proteins in this size range include, without limitation, the following: LHRH; LHRH analogs such as buserelin, gonadorelin, nafarelin and leuprolide: insulin; insulotropin; calcitonin; octreotide; endorphin; TRH; NT-36 (chemical name is N=[[(s)4-oxo-2-azetidinyl]carbonyl]-L-histidyl-L-prolinamide); liprecin; pituitary hormones such as HGH, HMG and desmopressin acetate; follicle luteoids; aANF; growth factors such as growth factor releasing factor (GFRF or GHRH); bMSH; somatostatin; bradykinin; somatotropin; platelet-derived growth factor; asparaginase; chymopapain; cholecystokinin; chorionic gonadotropin; corticotropin (ACTH); erythropoietin; epoprostenol (platelet aggregation inhibitor); glucagon; HCG; hirulog; hyaluronidase; interferon; interleukins; menotropins (urofollitropin (FSH) and LH); oxytocin; streptokinase; tissue plasminogen activator: vasopressin; desmopressin; ACTH analogs; ANP; ANP clearance inhibitors; angiotensin II antagonists: antidiuretic hormone agonists; antidiuretic hormone antagonists: bradykinin antagonists: CD-4; ceredase; CSFs; enkephalins; FAB fragments; IgE peptide suppressors; IGF-1; neurotrophic factors; colony stimulating factors: parathyroid hormone and agonists; parathyroid hormone antagonists: prostaglandin antagonists; pentigetide; protein C; protein S; renin inhibitors; thymosin alpha-1; thrombolytics; TNF; vaccines; vasopressin antagonist analogs; alpha-1 antitrypsin (recombinant); and TGF-beta.

Electrotransport devices generally require a reservoir or source of the agent, or a precursor of such agent, that is to be delivered into the body by electrotransport. Examples of such reservoirs or sources of, preferably ionized or ionizable, agents include a pouch as described in Jacobsen U.S. Pat. No. 4,250,878, or a pre-formed gel body as disclosed in Webster U.S. Pat. No. 4,383,529. Such reservoirs are electrically connected to the anode or the cathode of an electrotransport device to provide a fixed or renewable source of one or more desired therapeutic species.

Recently, a number of U.S. patents have issued in the electrotransport field, indicating a continuing interest in this mode of drug delivery. For example, Vernon et al U.S. Pat. No. 3,991,755, Jacobsen et al U.S. Pat. No. 4,141,359, Wilson U.S. Pat. No. 4,398,545, and Jacobsen U.S. Pat. No. 4,250,878 disclose examples of electrotransport devices and some applications thereof.

More recently, electrotransport delivery devices have become much smaller, particularly with the development of miniaturized electrical circuits (e.g., integrated circuits) and more powerful light weight batteries (e.g., lithium batteries). The advent of inexpensive miniaturized electronic circuitry and compact, high-energy batteries has meant that the entire device can be made small enough to be unobtrusively worn on the skin of the patient, under clothing. This allows the patient to remain fully ambulatory and able to perform all normal activities, even during periods when the electrotransport device is actively delivering drug.

Nevertheless, some limitations still remain, restricting the wider application of this valuable technique. One such limitation is the size and cost of electrotransport delivery devices. In particular, the batteries needed to power electrotransport devices comprise a significant contribution to the overall size and weight, as well as the cost, of these smaller, patient-worn electrotransport delivery devices. A reduction in the number and/or cost of these batteries would allow electrotransport drug delivery devices to be made smaller and at lower cost.

One method of reducing the number of batteries used to power an electrotransport device is to use a voltage boosting circuit. Boosting circuits are well known in the electrical arts. Conventional boosting circuits take an input voltage (e.g., 3.0 volts) and boost it by a predetermined multiple (e.g., ×2) to give a "boosted" output voltage (e.g., 6.0 v=3.0 v×2). Voltage boosting circuits have been used in transdermal electrotransport delivery devices. See Maurer et al U.S. Pat. No. 5,254,081 (at column 2, lines 34-39).

These circuits allow an electrotransport device to deliver a predetermined level of electric current with fewer batteries, or battery(ies) of lower voltage, than would otherwise be needed without the use of a boosting circuit. Thus, conventional boosting circuits help reduce the size and cost of an electrotransport delivery device by requiring fewer, and/or lower voltage, batteries to power the device.

The problem of reducing the cost of the power supply for an electrotransport delivery device is complicated by the fact that the electrical resistance of the patient body surface (e.g., skin) is not constant during electrotransport delivery. Since the voltage (V) necessary to drive a particular level of electric current (i) through the patient's skin is proportional to the resistance (R) of the skin (i.e., according to Ohm's Law wherein $V=iR_{skin}$), the voltage requirements of the power supply are not constant during electrotransport delivery. For example, when electrotransport administration is begun, the patients initial skin resistance is relatively high, requiring the power supply to produce relatively high voltage to deliver a predetermined level of electrotransport current. However, after several minutes (i.e., after about 1 to 30 minutes of current being applied through the skin) the skin resistance drops, such that the voltage requirement needed to deliver a particular level of electric current becomes significantly less than the voltage required at the start of electrotransport delivery. See for example Haak et al U.S. Pat. No. 5,374,242 which discloses the variable skin resistance and the use of 2 or more batteries connected either in parallel or in series to accommodate the changing skin resistance.

Although conventional voltage boosting circuits can supply the output voltage necessary to accommodate the high initial skin resistance, they reduce the efficiency of the apparatus and require more battery output voltage during periods when the skin resistance is lower than the initial state, resulting in lower efficiency and increased battery size and costs.

Jacobsen et al U.S. Pat. No. 4,141,359, incorporated herein by reference, discloses a DC-DC converter having a transformer to inductively couple periodic variations of current in a primary coil to pulses of current in a secondary coil at a fixed voltage multiple of the primary power supply. These pulses of secondary coil current are conducted through the skin by therapeutic electrodes. The average, or DC value of the secondary current is controlled by an error voltage and feed back circuit such that the average value of the secondary current is held constant.

One disadvantage of the Jacobsen circuit is that the peak value of the fixed and multiplied voltage appears directly across the electrodes. The peak voltage is unnecessary for conditions where the skin resistance is low, and results in unnecessarily high current pulses of therapeutic current and possible adverse effects on the skin.

DESCRIPTION OF THE INVENTION

It is an aspect of the present invention to provide a method of operating with increased efficiency an electrotransport agent delivery device having a voltage boosting circuit.

It is another aspect of the present invention to provide a method of operating an electrotransport agent delivery device in which the power supply voltage is boosted to a level which is optimally suited to the conditions (e.g., skin resistance) of agent delivery.

The present invention provides a method for operating an electrotransport agent delivery device having a voltage boosting circuit which boosts the power supply (e.g., battery) output voltage, in which boosting circuit the boost multiple is automatically controlled in response to the skin resistance of the patient. The device is adapted to deliver a therapeutic agent through an animal body surface (e.g., human skin) by electrotransport. The device has a source of electrical power (e.g., one or more batteries) with an output voltage. The power source output voltage is boosted with a voltage booster having an adjustable boost multiple to provide a working voltage. A body surface parameter selected from the electrical resistance of the body surface, the voltage drop across the body surface and/or the current applied through the body surface is sensed and the boost multiple is adjusted based upon the sensed body surface parameter to achieve an adjusted working voltage. By adjusting the boost multiple based upon the sensed body parameter (e.g., skin resistance), the device applies only that level of voltage which is needed to deliver a predetermined level of electrotransport current, without excess voltage being consumed by the boost circuit. Thus, the method of the present invention provides increased efficiency in the operation of an electrotransport delivery device.

BRIEF DESCRIPTION OF DRAWINGS

The above and other features, aspects, and advantages of the present invention will become apparent from the following written description and drawings, in which.

MODES FOR CARRYING OUT THE INVENTION

Figure 1:
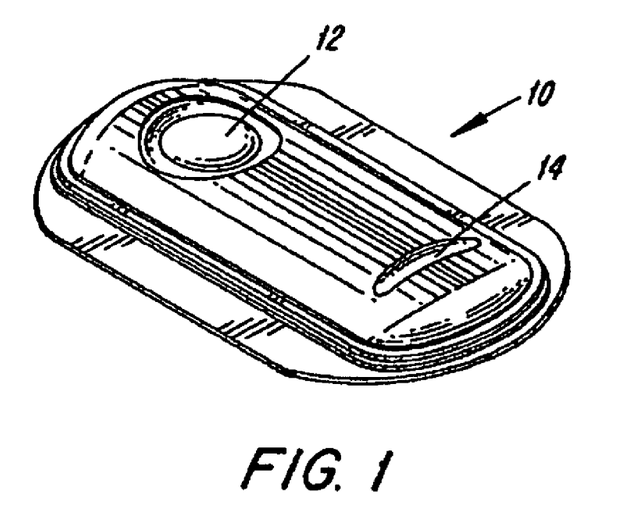
FIG. 1 is a perspective view of an electrotransport drug delivery device of this invention.
Figure 2:
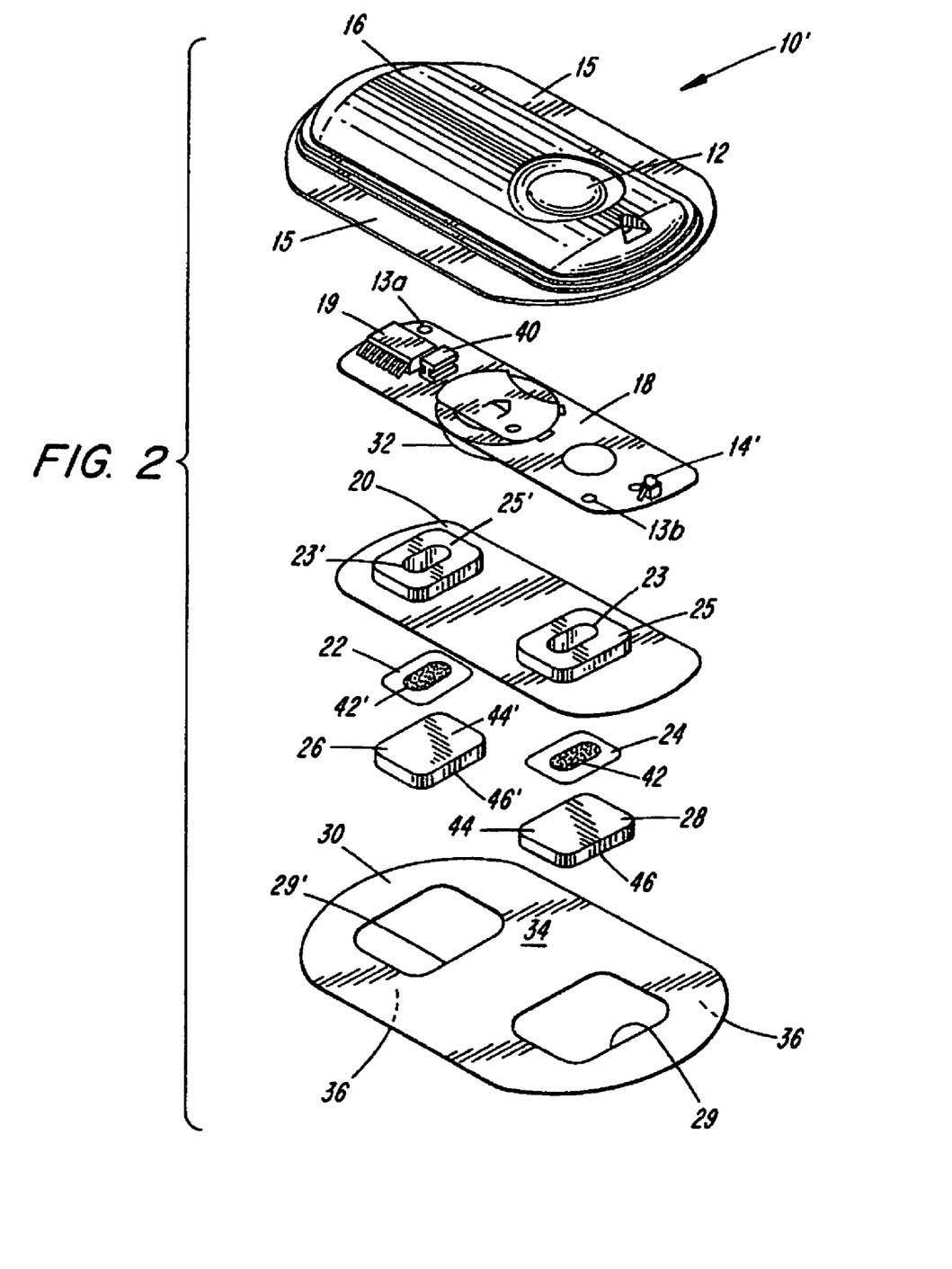
FIG. 2 is an exploded view of an electrotransport device of this invention.

The electronic circuit of the present invention can be used in substantially any electrotransport delivery device although the circuitry has particular utility in those devices adapted to deliver agents transdermally by electrotransport. Examples of electrotransport delivery devices which can be used with the circuitry of the present invention are illustrated in FIGS. 1 and 2. With reference to FIG. 1, there is shown a perspective view of an electrotransport device 10 having an optional activation switch in the form of a push button switch 12 and an optional light emitting diode (LED) 14 which turns on when the device 10 is in operation.

FIG. 2 is an exploded view of a second device 10' of this invention. The device 10' of FIG. 2 differs from device 10 of FIG. 1 in the location of LED 14'. LED 14' is located adjacent button switch 12 on one end of device 10' in this embodiment of the invention. Device 10' comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10' on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 2) passing through openings 13a and 13b. The ends of the posts are heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10'.

The device 10' is generally comprised of battery 32, electronic circuitry 19,40, electrodes 22,24, and drug/chemical reservoirs 26,28, all of which are integrated into a self-contained unit. The outputs (not shown in FIG. 2) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30.

Upon depression of push button switch 12, the electronic circuitry on circuit board assembly 18 delivers a predetermined DC current to the electrodes/reservoirs 22,26 and 24,28 for a delivery interval of predetermined length. Preferably, the device transmits to the user a visual and/or audible confirmation of the onset of the drug delivery by means of LED 14' becoming lit and/or an audible sound signal from, e.g., a "beeper". Drug is thereby delivered from one of reservoirs 26,28 and through the patient's skin by electrotransport.

Anodic electrode 22 is preferably comprised of silver and cathodic electrode 24 is preferably comprised of silver chloride. Both reservoirs 26 and 28 are preferably comprised of polymer hydrogel materials. Electrodes 22,24 and reservoirs 26,28 are retained by lower housing 20. One of reservoirs 26,28 is the "donor" reservoir and contains the therapeutic agent (e.g., a drug) to be delivered and the other reservoir typically contains a biocompatible electrolyte.

The push button switch 12, the electronic circuitry on circuit board assembly 18 and the battery 32 are adhesively "sealed" between upper housing 16 and lower housing 20. Upper Housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10' is preferably water resistant (i.e., splash proof) and is most preferably waterproof. The system has a low profile that easily conforms to the body thereby allowing freedom of movement at, and around, the wearing site. The reservoirs 26,28 are located on the skin-contacting side of the device 10' and are sufficiently separated to prevent accidental electrical shorting during normal handling and use.

The device 10' adheres to the patient's body surface (e.g., skin) by means of a peripheral adhesive 30 which has upper side 34 and body-contacting side 36. The adhesive side 36 has adhesive properties which assures that the device 10' remains in place on the body during normal user activity, and yet permits reasonable removal after the predetermined (e.g., 24-hour) wear period. Upper adhesive side 34 adheres to lower housing 20 and retains the electrodes and drug reservoirs within housing depression 25, 25' as well as retains lower housing 20 attached to upper housing 16.

The push button switch 12 is conveniently located on the top side of device 10' and is easily actuated through clothing. A double press of the push button switch 12 within a short time period, e.g., three seconds, is preferably used to activate the device for delivery of drug, thereby minimizing the likelihood of inadvertent actuation of the device 10'.

Figure 3:
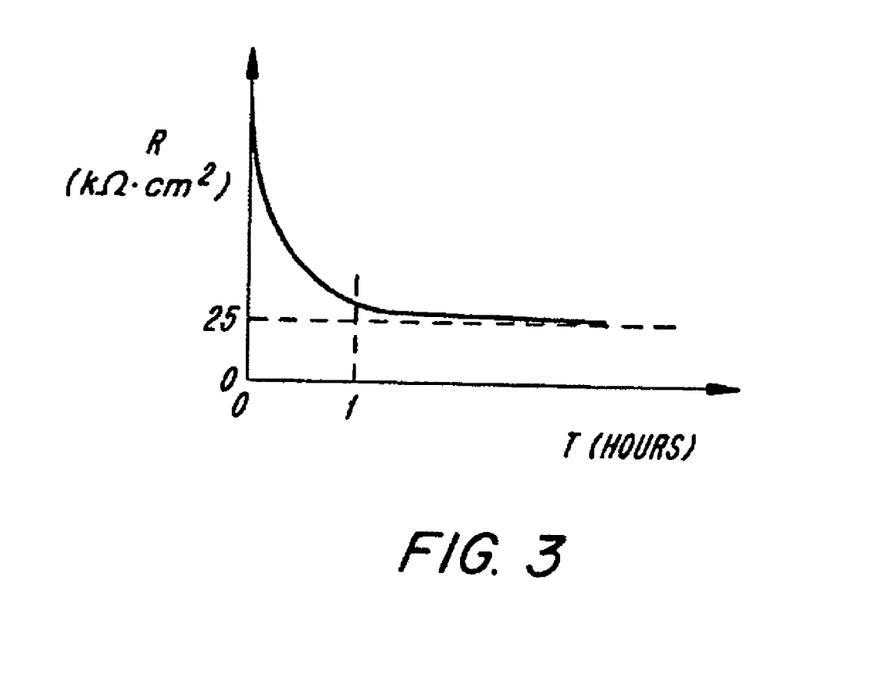
FIG. 3 is a graph illustrating the decline of patient skin resistance with time.

Upon first initiating agent delivery, the skin resistance of the patient is typically relatively high, whereas after a period of time, the skin resistance drops appreciably. FIG. 3 illustrates this characteristic graphically, showing that the decline of skin resistance R is substantially asymptotic to a steady state value. For a discharge rate of 0.1 ma/cm², this steady state value is typically on the order of 20 to 30 k$\Omega$-cm², while the initial value of skin resistance is several or many times as much.

In prior art electrotransport delivery devices, the voltage of the power supply and/or the boost multiple of the voltage boosting circuit, was/were chosen large enough to overcome the high skin resistance present at the start of operation. However, once operation had reached steady state, with the attendant drop in skin resistance, the prior art devices had excess working voltage. In certain prior art devices, the applied voltage needed to deliver a particular current at steady state operation was one half or less of the voltage required to deliver that same level of current at the start of electrotransport delivery. Accordingly, these prior art devices were not very cost effective because of the voltage wasted in the voltage boosting circuit once the skin resistance dropped from its initial high level.

Figure 4:
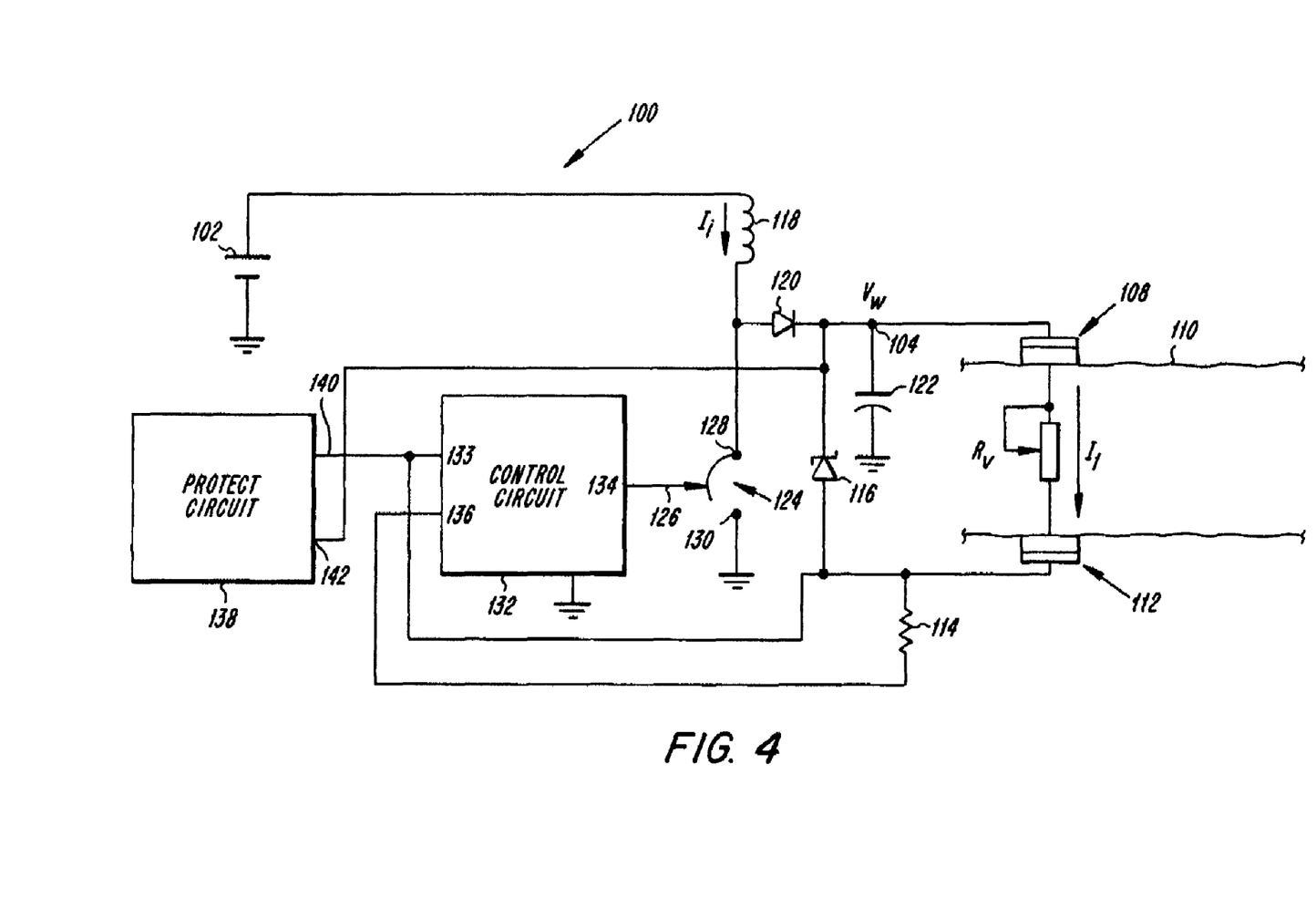
FIG. 4 is a schematic diagram of an adjustable voltage boosting circuit of this invention.

FIG. 4 illustrates a schematic diagram of a voltage boosting electrotransport circuit 100 with an adjustable boost multiple that is adjusted according to the sensed therapeutic load current level in accordance with the present invention. This permits more efficient use of batteries and results in significant size and cost savings when compared to the just-described prior art. The circuit 100 includes a power source in the form of a battery 102, and a voltage controlled electrical junction 104 electrically connected to an electrode assembly 108. The electrode assembly 108 is attached to one region of an animal body 110 by conventional means such as adhesive, straps, belts or the like. The animal body surface is shown schematically as a variable resistance load, $R_V$, to indicate the variation of load resistance typical of the skin when applying electric current $I_I$ therethrough.

An electrode assembly 112 is similarly attached to another region of the animal body 110. The electrode assembly 112 is connected to a series current sensing resistor 114. The electrodes 108, 112, the body surface 110 and sense resistor 114 form a load current path for conducting the load current, $I_I$. The electrode assemblies 108, 112 are equivalent to the electrode/reservoir combinations 22, 26 and 24, 28 shown in FIG. 2. At least one of the electrode assemblies 108, 112 contains a therapeutic agent (e.g., a drug salt) in a form (e.g., an aqueous solution) suitable for electrotransport delivery into the animal body 110.

An energy storage inductor 118 is connected between battery 102 and the anode of rectifying diode 120. The cathode of diode 120 is connected to the voltage controlled electrical junction 104. A filter capacitor 122 is connected between the junction 104 and system ground.

A controlled switch 124, having a control input 126, has one terminal 128 connected to the junction of the anode of diode 120 and the inductor 118 and another terminal 130 connected to system ground. The control input 126 can alternately open and close the switch 124 creating a low resistance connection between the terminals 128 and 130 thereby connecting or disconnecting the inductor through a low resistance path to system ground. The switch 124 may be an electronic switch device such as a bipolar or FET transistor.

A control circuit 132 has a control output 134 connected to switch control input 126. The control circuit 132 includes a feedback input 133 for controlling the control output 134 and a switch input 136.

Figure 5:
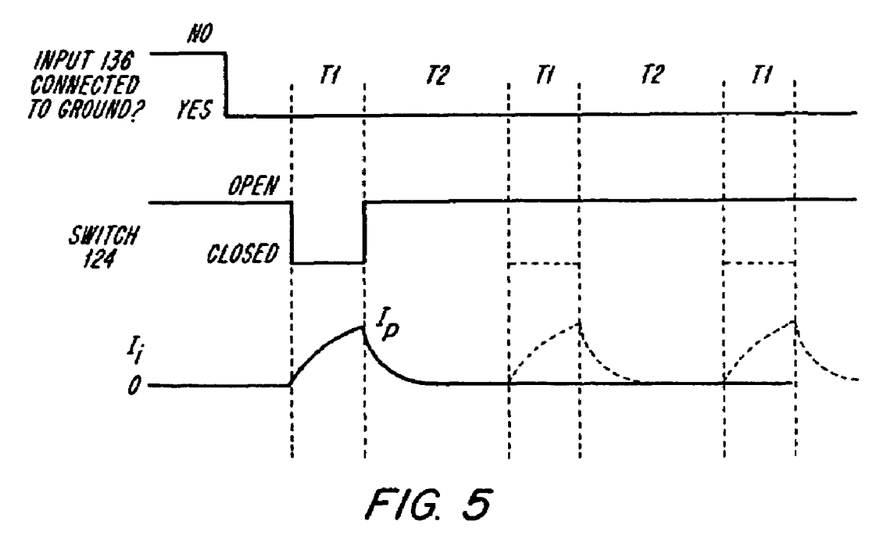
FIG. 5 is a timing diagram of the operation of the circuit of FIG. 4.

The operation of the adjustable voltage boost circuit 100 can be understood with reference to FIG. 5. After initiation of the circuit 100, for example, by means of a push button switch 12 illustrated in FIG. 1, the control circuit 132 is adapted to first connect the input 136 to system ground. This enables the sense resistor 114 to begin conducting load current, $I_I$, from the load 110.

The control circuit 132 is configured to then toggle the control output 134 so that the switch 124 connects the one end of the inductor 118 to ground for a period of time T1. During the time T1, the inductor current $I_i$, driven by the battery 102, increases to a maximum value, $I_p$.

At the end of time T1, the control circuit is adapted to change output 134 to toggle switch input 126 again which opens the switch 124 for a time period, T2. During T2, the inductor current, $I_i$, will not flow toward ground, but is forced to conduct through the diode 120 into the electrical junction 104. The filter capacitor 122 provides a low impedance path for the instantaneous current, $I_i$, which then decays toward zero during the time, T2, as the voltage at electrical junction 104 is boosted by the charging of the capacitor 122.

During the time T1, the inductor 118 stores energy by charging with the current, $I_i$. During the period T2, the inductor 118 discharges energy into the filter capacitor 122 through the diode 120. The inductor 118 thereby transfers energy from the battery 102 into the capacitor 122 with low loss, limited only by the diode 120 drop and the negligible series resistance of the inductor 118, battery 102 and the electrical connections. Thus, the energy source for load current $I_I$ is not directly the battery 102 but rather either the capacitor 122 (i.e., during time T1) or a combination of the capacitor 122 and inductor 118 (i.e., during time T2).

The control circuit 132 is adapted to repeat the T1, T2 cycle indefinitely or when stopped as described below. The voltage, $V_w$, at the junction 104 is thereby boosted to an adjustable multiple of the battery 102 voltage depending on the values of the time periods T1 and T2. The boost multiple thus can be adjusted by adjusting the values of T1 and T2.

Dotted lines in FIG. 5 indicate missing or delayed pulses as controlled by the control circuit 132. This may occur when pulses are not necessary to replace charge depleted from the capacitor 122, for example, when the therapeutic current, $I_I$, demanded is relatively low. The dotted lines in FIG. 5 indicate that the boost multiple control means may be by pulse width modulation (PWM), pulse frequency modulation (PFM), pulse skipping, or some combination thereof.

The adjustable working voltage, $V_w$, causes the load current, $I_I$, to flow through the animal body load 110, through the sense resistor 114 and into the switch input 136, to ground.

The feedback input 133 senses the voltage across the sense resistor 114 caused by the load current, $I_I$. The control circuit 132 is adapted to respond to the feedback input 133 to boost the working voltage, $V_w$, by adjusting the time periods, T1 and T2. This is accomplished by comparing the voltage sensed at input 133 with a set reference voltage within control circuit 132. If the voltage sensed at input 133 is less than the reference voltage, then control ciruit 132 opens and closes switch 124 at a high frequency until Vw is boosted to the appropriate level. In general, the longer switch 124 is closed (ie, the longer is T1), the greater the voltage which is developed in inductor 118 and the greater the boost multiple. The battery 102 voltage can be boosted by reason of the inductor 118. The voltage developed in the inductor 118 is equal to the inductance value (L) multiplied by the rate at which current flows through the inductor:

$$V_{ind} = L(dI_i/dt)$$

Thus, out of inductor 118 comes a higher voltage (which voltage is determined in part by the inductance value of inductor 118 and in part by the rate of current flow through inductor 118 which is controlled by the values of T1 and T2) at a lower current since the power into inductor 118 must equal the power out of inductor 118.

The control circuit 132 is additionally adapted such that, in combination with the values of the inductor 118, the value of the load resistance 110 and the capacitance value of the capacitor 122, the time periods, T1, T2, are arranged in response to the voltage at the feedback input 133 such that filter capacitor 122 smooths and adjusts the voltage $V_w$, to provide a load current, $I_f$, of an essentially constant (DC) current of predetermined value.

The electrode assemblies 108 and 112, and thus the animal body 110, are not exposed to high peak voltages as in the prior art, but instead experience only the minimum, constant value sufficient to drive the desired load current $I_f$.

The time periods T1 and T2 are adjusted by the control circuit 132 to boost $V_w$ to the minimum absolute value to provide the load current $I_f$ to maintain a desired predetermined value. If the resistance of the load 110 is too high to allow the predetermined value of $I_f$ to be attained without having $V_w$ exceed a safe level, a voltage limiting device, such as a zener diode 116 connected across the electrode assemblies 108 and 112, limits the voltage applied to load 110. A typical safe maximum limiting value for $V_w$ is about 24 volts. Other values of limiting voltage can be achieved by zener diodes 116 having different breakdown voltages, or by using other protection means as described further below.

Once the resistance of the load 110 decreases sufficiently to allow the load current, $I_f$, to reach the desired predetermined level at the maximum safe voltage, the control circuit 132 will respond to the feedback at feedback input 133 and will adjust T1 and T2 to boost $V_w$ to a multiple just sufficient to maintain the current at the predetermined level independent of further resistance decreases.

The working voltage, $V_w$, at the controlled electrical junction 104 is thus boosted to a boost multiple of the battery 102 voltage just sufficient to maintain the load current, $I_f$, at the predetermined value as long as the load voltage is less than the limiting voltage set by the zener diode 116.

The low loss transfer of energy from the battery 102 to the load 110 and capacitor 122 maximizes the useful life of the battery 102, for a given battery capacity. This allows smaller batteries to be used for a given therapeutic regimen, or extends the lifetime of therapeutic treatment at a given cost.

The predetermined current applied across load 110 may be constant or varying with time. In either event, the control circuit 132 is provided with means for establishing a predetermined current-time profile to be applied. This may be accomplished by means well known in the art, such as a differential comparator having one input connected to the sense resistor 114, a constant reference voltage connected to of the other input, or having the other input connected to the output of a D to A converter driven by a clocked ROM having a pre-programmed pattern (not shown in FIG. 4).

The circuit 100 may also be provided with a protection circuit 138. The protection circuit 138 has high impedance and low impedance checking functions and includes an input 140 which senses the voltage drop across load 110 and compares the sensed voltage drop against a preset minimum limit therefor. Circuit 138 also includes an input 142 which senses the current $I_f$ applied through load 110 and compares the sensed current against a preset maximum limit therefor. Protection circuits offering impedance checking and shut down protection are well known in the art. See, for example the protection circuits shown in FIG. 1 of Jacobsen et al U.S. Pat. No. 4,141,359 incorporated herein by reference.

The protection circuit 138 monitors the resistance of the load 110 by the voltage input 140 and the current input 142 and shuts down the voltage boosting function of the circuit 100 when the resistance of the load 110 exceeds a predetermined upper limit or decreases below a predetermined lower limit. Incorporation of the protection and shutdown circuit 138, of the type described in U.S. Pat. No. 4,141,359, into the booster circuit 100 is within the capability of a person having ordinary skill in the electrical arts.

In use, the electrode assemblies 108 and 112 are attached to the skin surface 110 by conventional means, and the therapeutic current is initiated, by a switch means (not shown) such as switch 12 shown in FIG. 1. The control circuit 132 begins controlling the on and off switching of switch 124. Repetitive pulses of inductor current, $I_i$, are alternately charged during the on time periods, T1, through the switch 124 to ground and discharged during the off time periods, T2 into the capacitor 122. These pulses of inductor current cause the voltage, $V_w$, to be multiplied by an adjustable boost multiple by adjusting the on and off times T1, T2 until the signal to feed back input 133 indicates the load current $I_f$ is in regulation.

Figure 6:
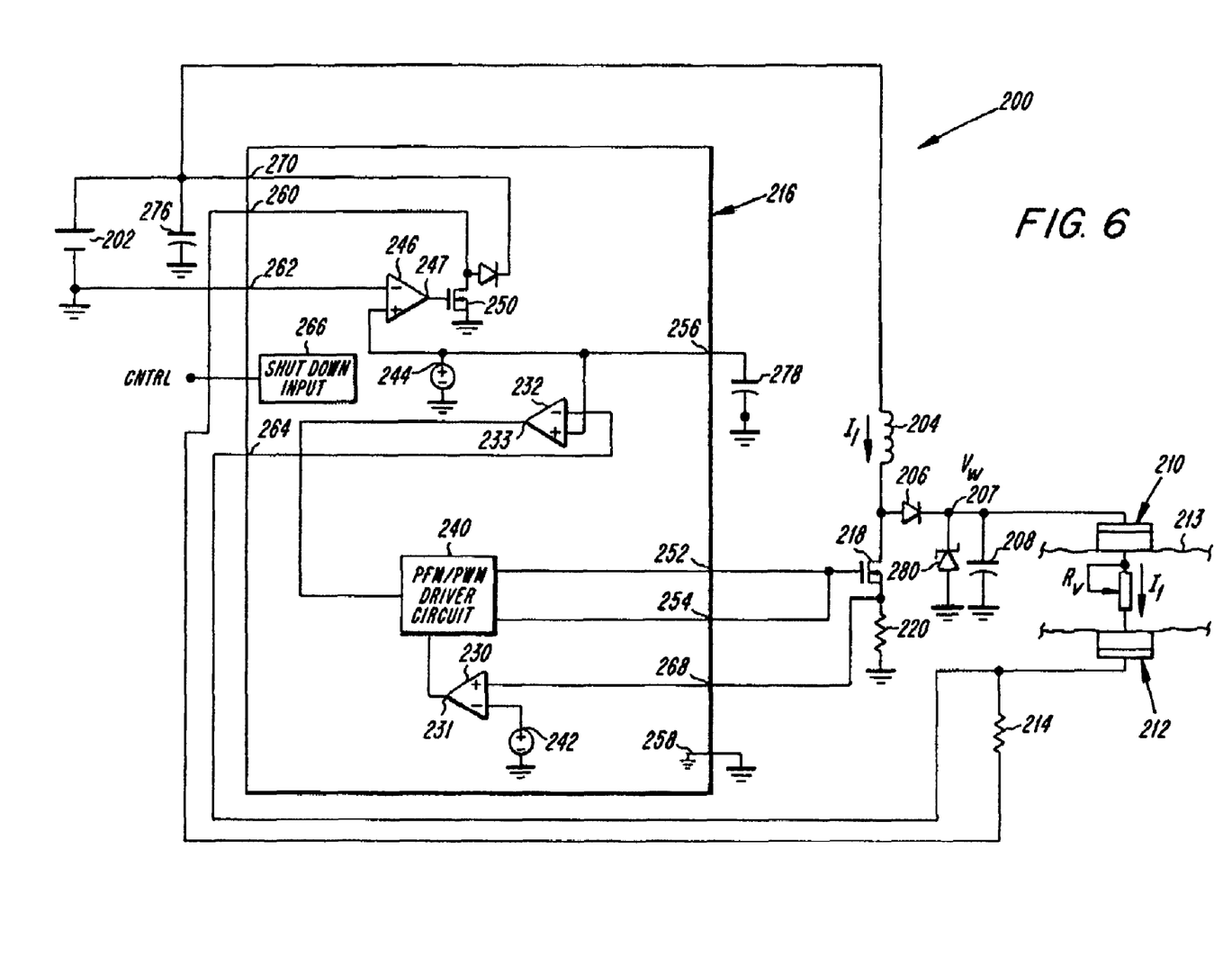
FIG. 6 is a schematic diagram of another adjustable voltage boosting circuit of this invention.

FIG. 6 shows another adjustable boost circuit 200 in accordance with this invention. The circuit 200 includes a battery 202, an inductor 204, a diode 206, a voltage controlled electrical junction 207, a low resistance filter capacitor 208, and electrode assemblies 210, 212 which are attached by conventional means to spaced apart regions of animal body 213. The animal body 213 is represented schematically as a variable load resistance $R_v$ to emphasize the fact that the resistance of the load 213 does vary with time and current.

At least one of the electrode assemblies 210, 212 contains a therapeutic agent in a form suitable for electrotransport delivery into the animal body 213.

The circuit 200 includes an N-channel field effect transistor (FET) switch 218, for switching inductor current $I_i$, an inductor current sense resistor 220, and a load current sense resistor 214. The circuit also includes a high efficiency, adjustable DC-DC step up controller 216. A preferred controller 216 is the Maxim MAX773 made by Maxim Integrated Products, Inc. of Sunnyvale, Calif.

FIG. 6 shows a simplified schematic of the MAX773 controller 216 which is sufficient for purposes of the present invention. A more detailed schematic of the MAX773 controller can be found in the MAX773 data sheet 19-0201; Rev 0; 11;93, incorporated herein by reference. A simplified block diagram version of the MAX773 data sheet is shown in FIG. 6. The controller 216 includes a reference voltage pin 256, a ground pin 258, a grounding switch input 260, a low level threshold input 262, a feed back input 264, a shut down input 266, a current sense input 268, and a power bus input 270.

Controller 216 also includes a first two-input comparator 230 having an output 231, a second two-input comparator 232 having an output 233, a first reference voltage 242, a second (e.g., 1.5 volt) reference voltage 244, a third two-input comparator 246 having an output 247, a PFM/PWM driver circuit 240 having a switch control output 252 and a switch control output 254, and a second N-channel FET switch 250.

Figure 7:
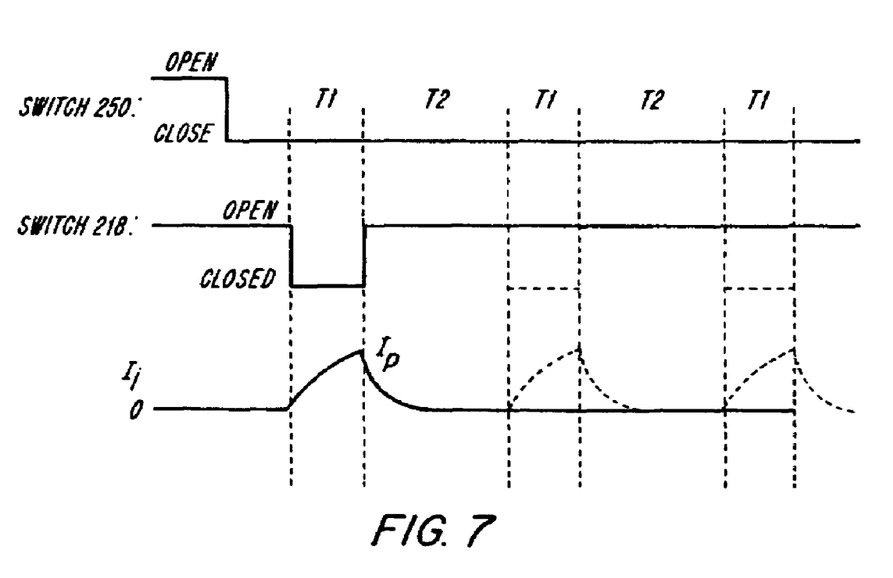
FIG. 7 is a timing diagram of the operation of the circuit of FIG. 6.

Operation of the circuit 200 can be understood by reference to FIGS. 6 and 7. The circuit 200 uses the controller 216 in a novel way to provide a high efficiency conversion of energy from the battery 202 into an adjustably boosted voltage $V_w$ at the voltage controlled electrical junction 207 and simultaneously controlling the load current $I_f$.

Unlike traditional pulse frequency (PFM) converters, which use an error voltage from a voltage divider circuit to control the output voltage of the converter to a constant value, controller 216 is connected to use the sense resistor 214 to generate an error voltage to control the average load current $I_f$. The MAX773 controller also operates with high frequencies, (up to 300 kHz) allowing the use of small external components.

With reference to FIG. 6, in accordance with this invention, a portion of the load current $I_f$ is fed back to the feed back input 264. The electrode assemblies 210 and 212 are attached to the animal body 213 which is represented as a variable resistance load.

The controller 216 is an integrated circuit having internal components connected by conductive traces formed during the integrated circuit manufacturing process. External pins are provided for electrical connection to external components by conventional printed circuit means such as plated or deposited copper or other conductors deposited and formed on insulating substrates. Reference to electrical connections in the description herein are understood to be internal or external as shown in FIG. 6. References to the components of the MAX773 controller circuit are illustrative for the purposes of describing the function of circuit 216.

One terminal of sense resistor 214 is connected to the feed back input 264. This same terminal of resistor 214 is also connected to the electrode assembly 212 for receiving the load current $I_f$. The other terminal of resistor 214 is connected to the input 260 of controller 216. The input 260 internally connects to the drain of the N-channel switch 250. The source of switch 250 connects to system ground. The gate of switch 250 connects to the output 247 of comparator 246. The inverting input of comparator 246 connects to the input pin 262. The input pin 262 is connected to system ground. The non-inverting input of comparator 246 is connected to the reference voltage 244. The reference voltage 244 also connects to the reference voltage pin 256. The comparator 246 is driven such that output 247 is always high. Switch 250 will therefore be driven to conduct the pin 260 to ground, sinking the load current $I_f$ to ground through the sense resistor 214.

The input 264 connects to the inverting input of comparator 232. The non-inverting input of comparator 232 is connected to the reference voltage 244. The output 233 of comparator 232 is connected to the PFM/PWM driver circuit 240.

The output 231 of comparator 230 is connected to the PFM/PWM driver circuit 240. The inverting input of comparator 230 is connected to the reference voltage 242. The non-inverting input of comparator 230 connects to the current sense input 268. Input 268 is connected to one terminal of inductor current sense resistor 220. The other terminal of resistor 220 connects to system ground. The ground pin 258 of the controller 216 is also connected to system ground.

One output of the PFM/PWM driver circuit 240 connects to the output 252. The input 270 is connected to one terminal of the battery 202. The other terminal of the battery 202 is connected to system ground. One output of the PFM/PWM driver circuit 240 connects output 254. The outputs 252 and 254 are both connected to the gate of the external N-channel switch 218. The drain of the switch 218 is connected to a joint connection of one end of the energy storage inductor 204 and the anode of rectifying diode 206. The source of the switch 218 is connected to the one terminal of the inductor current sense resistor 220 which is connected to the current sense input 268.

The other terminal of the inductor 204 is connected to the power bus input 270 and to the terminal of the battery 202. A filter capacitor 276 is connected between the input 270 and ground. A filter capacitor 278 is connected between the voltage pin 256 and ground. The filter capacitors 276 and 278 have low dynamic impedance at the pulse frequencies of interest.

The cathode of diode 206 is connected to an electrical junction 207. The junction 207 is also connected to one terminal of a filter capacitor 208, the cathode of a zener diode 280 and the electrode assembly 210. The anode of the zener diode 280 and the other terminal of capacitor 208 are connected to ground. The junction 207 completes the circuit 200 which boosts the working voltage, $V_w$, at the junction 207 by an adjustable multiple of the voltage of the power source, ie, battery 202.

The zener diode 280 provides a means to limit the peak voltage across the electrode assemblies 210 and 212 and thus the maximum voltage experienced by the animal body load 213.

With reference to FIGS. 6 and 7, the operation of the adjustable voltage boost multiple circuit 200 can be understood. When power is applied by the battery 202 to input 270 and the input signal 266 is of the correct logic level, the controller 216 begins operating. Since input 262 is held low, and the non-inverting input of comparator 247 is at, e.g., 1.5 volts, from reference voltage 244, the output of the comparator 246 will be high. With a high voltage on the gate of the switch 250 the input 260 will be driven to ground by the drain of switch 250. This enables the resistor 214 to receive load current $I_f$ from the electrode assembly 212.

As with traditional PFM converters, the switch 218 is not turned on until the voltage comparator 232 senses the output current is out of regulation. However, unlike traditional PFM converters, the MAX773 uses the combination of the peak inductor current limit sense resistor 220, reference voltage 242 and comparator 230 along with the maximum switch on-time and minimum switch off-time generated by the PFM/PWM driver circuit 240; there is no oscillator. The typical maximum switch on-time, T1, is 16 micro seconds. The typical minimum switch off-time, T2, is 2.3 micro seconds.

Once off, the minimum off-time holds the switch 218 off for time T2. After this minimum time, the switch 218 either (1) stays off if the output current $I_f$ is in regulation, or (2) turns on again if the output current $I_f$ is out of regulation.

While the switch 218 is off, the inductor current $I_i$ flows through the diode 206 into the capacitor 208 at junction 207, replenishing any charge drawn off by the load 213. It can be seen that this method of switching the charging current $I_i$ provides an adjustable boost multiple of the battery 202 voltage to a working voltage $V_w$ at the junction 207, just sufficient to supply the desired constant current $I_f$. The peak voltage delivered by the inductor 204, will be just that required to overcome the diode drop of the diode 206 and the working voltage $V_w$ and thus minimizes energy loss from the battery 202.

The controller 216 circuitry allows the circuit 200 to operate in continuous-conduction mode (CCM) while maintaining high efficiency with heavy loads. When the power switch 218 is turned on, it stays on until either (1) the maximum on-time turns it off (typically 16 microseconds later), or (2) the inductor current $I_i$ reaches the peak current limit $I_p$ set by the inductor current limit resistor 220, the reference voltage 242 and comparator 230. In this event, the on time will be less than the maximum on time, T1. Limiting the peak inductor current, to a predetermined maximum, $I_p$, avoids saturating the inductor 204 and allows the use of smaller inductor values, thus smaller components.

If the average load current $I_f$ is below the desired value as set by the value of reference voltage 244 and the value of sense resistor 214 through the relation $$V_{ref} > I_f * R_s$$

then the PFM/PWM driver circuit 240 will automatically adjust the on time, T1 and off time, T2 and alternately turn the switch 218 on and off until the load current I$_l$ is in regulation.

Operation of the adjustable boost multiple circuit 200 may be initiated by connecting the shut down input 266 to a logic high level by switch means, such as switch 12 shown in FIG. 1. When shut down input 266 is high, the MAX773 circuit enters a shut down mode. In this mode the internal biasing circuitry is turned off (including the reference), switch 250 enters a high impedance state and the working voltage V$_w$ falls to a diode drop below the battery 202 voltage (due to the DC path through the inductor 204 from the battery 202 to the electrode assembly 210). The supply current from the battery 202 becomes equal to V$_w$/I$_l$. However, no current path is available with the high impedance state of switch 250 and the load current I$_l$ is zero.

In alternate embodiments of this invention, the current I$_l$ may be programmed to follow a predetermined profile by programming the value of the load current sense resistor 214. The resistor 214 value may be programmed by switching additional resistors in parallel or series with the load current I$_l$. Such switching control means are well known in the art.

Although this invention has been described with some particularity in respect to embodiments thereof which, taken together, comprise the best mode known to the inventors for carrying out their invention, many changes could be made, and many alternative embodiments could thus be derived without departing from the scope of the invention. Consequently, the scope of the invention is to be determined only from the following claims.

What is claimed is:

1. A method of regulating an electrotransport system for delivering a beneficial agent through an animal skin surface having a variable resistance load, the electrotransport system having a first electrode assembly and a second electrode assembly in contact with the animal skin surface, the method comprising:
    (a) supplying a first voltage;
    (b) boosting the first voltage to create an adjustable working voltage that is an adjustable multiple of the first voltage, wherein the boosting of the first voltage depends on an adjustable first time period T1 during which energy is stored and an adjustable second time period T2 during which the stored energy is discharged;
    (c) providing the adjustable working voltage to an electrical junction coupled to the first electrode assembly to cause a load current to flow through the variable resistance load and through a current sensing resistor coupled in series to the second electrode assembly;
    (d) sensing a second voltage created across the current sensing resistor by the load current;
    (e) comparing the second voltage to a reference voltage;
    (f) adjusting the first time period T1 and the second time period T2 if the second voltage is less than the reference voltage such that when the first voltage is boosted based on the first time period T1 and the second time period T2 in a repeat of step (b), the adjustable working voltage provided in a repeat of step (c) would be at a level that would cause the load current to flow at a predetermined value; and
    (g) repeating steps (b), (c), (d), (e), and (f) such that at steady state the load current flowing through the variable resistance load is maintained at the predetermined value.

2. The method of claim 1, wherein the adjustable working voltage is repeatedly boosted to a minimum absolute value to maintain the load current at the predetermined value.

3. The method of claim 2, further comprising limiting a voltage applied to the variable resistance load to a predetermined safe level if the adjustable working voltage exceeds the predetermined safe level.

4. The method of claim 1, further comprising monitoring a resistance of the variable resistance load and stopping step (g) if the resistance of the variable resistance load exceeds a predetermined upper limit or falls below a predetermined lower limit.

5. The method of claim 1, wherein the adjustable working voltage is repeatedly boosted to cause the load current to follow a predetermined current-time profile.

* * * * *